United States Patent [19]

Schröder

[11] Patent Number: 5,206,372

[45] Date of Patent: Apr. 27, 1993

[54] PREPARATION OF 2-CHLOROPYRIDINE DERIVATIVES

[75] Inventor: Ludwig Schröder, Ingelheim am Rhein, Fed. Rep. of Germany

[73] Assignee: Shell Research Limited, United Kingdom

[21] Appl. No.: 706,861

[22] Filed: May 29, 1991

[30] Foreign Application Priority Data

Jun. 5, 1990 [EP] European Pat. Off. ........ 90110636.9

[51] Int. Cl.$^5$ ................ C07D 213/71; C07D 213/56; C07D 401/04
[52] U.S. Cl. .................... 546/294; 546/250; 546/281; 546/316; 546/317; 546/323
[58] Field of Search ............. 546/250, 316, 317, 281, 546/294, 323

[56] References Cited

U.S. PATENT DOCUMENTS 4,080,336  3/1978  Said ..................... 546/316

FOREIGN PATENT DOCUMENTS

| | | | |
|---|---|---|---|
| 0313317 | 4/1989 | European Pat. Off. ........... | 544/318 |
| 0372654 | 6/1990 | European Pat. Off. ........... | 546/250 |
| 2611601 | 9/1977 | Fed. Rep. of Germany ...... | 546/316 |
| 2713346 | 10/1977 | Fed. Rep. of Germany ...... | 546/316 |
| 3342538 | 5/1984 | Fed. Rep. of Germany ...... | 546/114 |
| 2285379 | 4/1976 | France ............................... | 544/159 |
| 0047132 | 4/1966 | German Democratic Rep. ................................... | 546/316 |
| 61-239246 | 10/1986 | Japan .................................. | 548/251 |
| 8804297 | 6/1988 | PCT Int'l Appl. ................. | 546/294 |
| 1521997 | 8/1978 | United Kingdom ............... | 546/316 |

Primary Examiner—Alan L. Rotman

[57] ABSTRACT

Certain 2-chloropyridine derivatives, which are useful as starting materials for the preparation of various herbicides and fungicides, are prepared by cyclization of 1,3-butadiene derivatives in the presence of hydrogen chloride.

9 Claims, No Drawings

PREPARATION OF 2-CHLOROPYRIDINE DERIVATIVES

This invention relates to a process for the preparation of certain 2-chloropyridine derivatives, in particular, 3-amido and 3-alkylsulphonyl derivatives, which are useful as starting materials for the preparation of various herbicides and fungicides. Examples of such pesticides are disclosed in European published application no. EP 0313317 and WO 88/04297.

Various processes have been described for the preparation of such derivatives. However, these have not proved to be entirely satisfactory for various reasons. For instance, copending European application no. 0372654 A2 describes the preparation of 2-chloropyridine-3-carboxylic acid esters from the corresponding butadiene derivatives. However, it is not possible to convert these esters directly to the corresponding amide by reaction with an appropriate amine as the amine preferentially displaces the chloro group to form 2-aminopyridine-3-carboxylic acid esters. Instead, it is first necessary to convert the ester to the corresponding acid and then convert the acid to the corresponding acid chloride prior to reaction with an appropriate amine to obtain the desired amide. Moreover, this process not only necessitates the inclusion of two additional stages in the reaction but it also requires the use of chlorinating agents which are either aggressive, such as thionyl chloride, phosgene or phosphorus halides, or expensive, such as oxalyl chloride. Similarly, it is not possible to convert 2-chloropyridinecarboxylic acid esters directly into 2-chloro-3-alkylsulphonylpyridines.

It has now been discovered that certain 2-chloropyridine derivatives can be prepared in high yield directly from an appropriate butadiene derivative. According to the present invention there is therefore provided a process for the preparation of a compound of the general formula

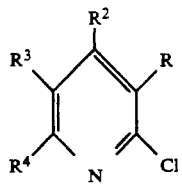

(I)

in which R represents a group —CONR¹R⁷ or —SO₂R⁸ where R¹ and R⁷ independently represent a hydrogen atom or an optionally substituted alkyl or aryl group and R⁸ represents an optionally substituted alkyl or aryl group; R² represents a hydrogen atom or an optionally substituted alkyl or alkoxy group; and R³ and R⁴ independently represent a hydrogen atom or an optionally substituted alkyl or alkoxy group or R³ and R⁴ together represent an optionally substituted alkylene group; characterised in that a compound of the general formula

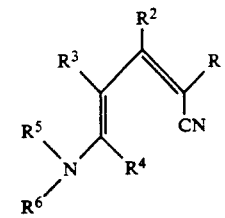

(II)

in which R, R², R³, and R⁴ are as defined above and R⁵ and R⁶ independently represent a hydrogen atom or an optionally substituted alkyl, alkenyl, alkynyl, cycloalkyl or aryl group or R⁵ and R⁶ together with the interjacent nitrogen atom represent an optionally substituted heterocyclic ring, is reacted with hydrogen chloride in the presence of a solvent.

When the compounds of formula I or formula II contain an alkyl, alkenyl or alkynyl substituent group, this may be linear or branched and may contain up to 10, preferably up to 6 and especially up to 4, carbon atoms. A cycloalkyl group may contain from 3 to 10, preferably 3 to 6, carbon atoms. An alkylene group may contain 1 to 8, preferably 2 to 6, carbon atoms. An aryl group may be any aromatic hydrocarbon group, especially a phenyl or naphthyl group. A heterocyclic ring may be any saturated or unsaturated ring system containing at least one nitrogen atom and may also contain an additional heteroatom, 5- and 6-membered rings being especially preferred.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms.

It is preferred that, when R represents the —CONR¹R⁷, R¹ and R⁷ independently represent a hydrogen atom or a $C_{1-10}$alkyl or phenyl group, each group being optionally substituted by one or more substituents selected from halogen atoms, $C_{1-4}$alkyl and $C_{1-4}$ alkoxy groups.

More preferably, R¹ and R⁷ independently represent a $C_{1-4}$ alkyl group.

It is also preferred that, when R represents the group —SO₂R⁸, R⁸ represents a $C_{1-10}$ alkyl group optionally substituted by one or more substituents selected from halogen atoms, $C_{1-4}$ alkyl and $C_{1-4}$ alkoxy groups.

More preferably, R⁸ represents a $C_{1-4}$ alkyl group.

Preferably, R² represents a hydrogen atom or a $C_{1-6}$ alkyl or $C_{1-6}$ alkoxy group, each group being optionally substituted by one or more halogen atoms.

More preferably, R² represents a $C_{1-4}$ alkyl or $C_{1-4}$ alkoxy group or, most preferably, a hydrogen atom.

It is preferred that R³ and R⁴ independently represent a hydrogen atom or a $C_{1-6}$ alkyl or $C_{1-6}$ alkoxy group, each group being optionally substituted by one or more halogen atoms, or $R^3$ and $R^4$ together represent an alkylene group —$(CH_2)_n$—, where n is an integer from 1 to 8, optionally substituted by halogen atoms.

More preferably, $R^3$ and $R^4$ independently represent a $C_{1-4}$alkyl or $C_{1-4}$alkoxy group or, most preferably, a hydrogen atom, or $R^3$ and $R^4$ together represent an alkylene group —$(CH_2)_n$—, where n is an integer from 2 to 6.

It is also preferred that $R^5$ and $R^6$ independently represent a hydrogen atom or a $C_{1-10}$alkyl, $C_{2-10}$alkenyl, $C_{2-10}$alkynyl, $C_{3-10}$cycloalkyl or phenyl group, each group being optionally substituted by one or more substituents selected from halogen atoms, $C_{1-4}$alkyl or $C_{1-4}$ alkoxy groups, or $R^5$ and $R^6$ together with the interjacent nitrogen atom represent a 5- or 6-membered heterocyclic ring optionally substituted by one or more substituents selected from halogen atoms, $C_{1-4}$alkyl and $C_{1-4}$alkoxy groups.

More preferably, $R^5$ and $R^6$ independently represent a hydrogen atom or a phenyl or, most preferably, a $C_{1-4}$alkyl group or $R^5$ and $R^6$ together with the interjacent nitrogen atom represent a 5- or 6-membered heterocyclic ring, preferably, a pyrrolidine ring.

Most preferably, $R^1$, $R^5$, $R^6$ and $R^7$ represent a methyl group and $R^2$, $R^3$ and $R^4$ represent a hydrogen atom and $R^8$ represents a propyl group.

The use of a particular solvent does not appear to be critical to the reaction and polar and non-polar solvents may be used as well as mixtures of these solvents. Suitable solvents include lower alcohols such as methanol, ethanol, n-propanol, isopropanol, n-butanol or isobutanol, lower ketones such as acetone or ethyl methyl ketone, chlorinated hydrocarbons such as dichloromethane or 1,2-dichloroethane, or aromatic hydrocarbons such as benzene or toluene. Particularly preferred solvents are 1,2-dichloroethane, toluene and isopropanol.

The reaction may be conveniently performed at a temperature in the range from 0° C. to 110° C., preferably in the range from 5° C. to 70° C. In practice, a temperature between 20° C. and 60° C. has proved especially suitable.

The preparation of compounds of formula I may be carried out with isolated intermediates of formula II which may, in turn, be prepared by processes analogous to known processes. However, it is especially advantageous to generate the intermediates in situ and to react them subsequently in a one-pot reaction with hydrogen chloride. The hydrogen chloride may be used in equimolar amounts or in excess, however, it is generally preferred to add it in excess.

Certain of the intermediates of formula II are novel per se, although JP 61239246 A2 discloses 1-cyano-1-(ethylsulphonyl)-4-(4-morpholinyl)-1,3-butadiene and FR 2285379 and Res. Discl., 149, (1976), pp.88–91 disclose 1-cyano-1-(methylsulphonyl)-4-(4-morpholinyl)-1,3-butadiene. Accordingly, the invention also provides compounds of formula II in which R, $R^2$, $R^3$, $R^4$, $R^5$ and $R^6$ are as previously defined with the proviso that when $R^2$, $R^3$ and $R^4$ simultaneously represent a hydrogen atom and $R^5$ and $R^6$ together with the interjacent nitrogen atom represent a 4-morpholinyl group then R does not represent a methylsulphonyl or ethylsulphonyl group.

The process according to the invention is further illustrated by the following examples.

EXAMPLE 1

Preparation of 2-chloropyridine-3-carboxylic acid N,N-dimethylamide (R=—$CONR^1R^7$; $R^1$=$R^7$=$CH_3$; $R^2$=$R^3$=$R^4$=H)

(a) Preparation of 1-cyano-1-dimethylaminocarbonyl-4-dimethylamino-1,3-butadiene.

3-Dimethylaminoacrolein (25 g, 0.25 mol) and cyanoacetic acid N,N-dimethylamide (28 g, 0.25 mol) were dissolved in toluene (250 ml) and piperidine (1 ml) and acetic acid (2.5 ml) were then added. The solution was heated under reflux in a water separator until no more water was formed (about 2 hours). The solution was then filtered and reduced to about 100 ml. On cooling, crystals formed which were filtered off under suction and dried to give 34 g 1-cyano-1- dimethylaminocarbonyl-4-dimethylamino-1,3-butadiene as yellow-brown crystals, m.pt. 149°–150° C.

(b) Preparation of 2-chloropyridine-3-carboxylic acid N,N-dimethylamide

The 1-cyano-1-dimethylaminocarbonyl-4-dimethylamino-1,3-butadiene (14.5 g, 0.075 mol) obtained in (a) above was dissolved in 1,2-dichloroethane (150 ml) and the resulting solution heated to 50° C. The solution was then stirred whilst hydrogen chloride gas was introduced. After a few minutes, a thick mass of crystals formed in the solution which later dispersed to leave a deep red solution. After about 6 hours, no more starting material could be detected. Nitrogen was then introduced to blow the excess hydrogen chloride gas out of the solution and the solution was then extracted with water (4×100 ml). The organic phase was then dried over sodium sulphate and reduced in a vacuum. The residue was then stirred in petroleum ether, filtered off under suction and dried to give 10 g 2-chloropyridine-3-carboxylic acid N,N-dimethylamide as pale yellowish crystals, m.pt. 70°–71° C. Yield: 72% of the theoretical.

EXAMPLE 2

Preparation of 2-chloro-3-isopropylsulphonylpyridine (R=—$SO_2R^8$; $R^8$=—$CH(CH_3)_2$: $R^2$=$R^3$=$R^4$=H)

(a) Preparation of 1-cyano-1-isopropylsulphonyl-4-dimethylamino-1,3-butadiene

3-Dimethylaminoacrolein (17 ml, 0.17 mol) and isopropylsulphonylacetonitrile (25 g, 0.17 mol) were dissolved in toluene (250 ml) and piperidine (1 ml) and acetic acid (2.5 ml) were then added. The solution was heated under reflux in a water separator until no more water was formed (about 3 hours). On cooling, crystals formed which were filtered off under suction and dried to give 26 g 1-cyano-1-isopropylsulphonyl-4-dimethylamino-1,3-butadiene as yellow-brown crystals, m.pt. 102°–104° C. The remaining toluene was then extracted with water (2×50 ml), dried over sodium sulphate and evaporated under vacuum to give about 15 g of a brown syrup. This was then purified over silica using ethyl acetate as eluant to give a further 8.8 g 1-cyano-1-isopropylsulphonyl-4-dimethylamino-1,3-butadiene crystals. Yield: 90.2% of the theoretical.

(b) Preparation of 2-chloro-3-isopropylsulphonylpyridine

The 1-cyano-1-isopropylsulphonyl-4-dimethylamino-1,3-butadiene (34 g, 0.15 mol) obtained in (a) above was dissolved in isopropanol (350 ml). The solution was then heated to reflux and saturated with dry hydrogen chloride. After about 20 hours, the solution was cooled and poured into water and crushed ice. This solution was then neutralised with sodium hydroxide solution and extracted with toluene (5×100 ml). The combined extracts were then evaporated and the remaining brown syrup purified over silica using 1:1 toluene:ethyl acetate as eluant to leave an oil which yielded 7 g 1-chloro-3-isopropylsulphonylpyridine as yellow crystals, m.pt. 82°–84° C., after stirring with petroleum ether. Yield: 51.5% of the theoretical.

I claim:

1. A process for the preparation of a compound of the formula

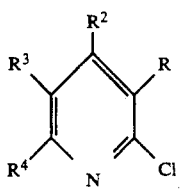
(I)

in which

R represents a group —CONR¹R⁷ or —SO₂R⁸ where R¹ and R⁷ independently represent a hydrogen or an optionally substituted $C_{1-10}$ alkyl or aryl group and R⁸ represents an optionally substituted $C_{1-10}$ alkyl or aryl group;

R² represents a hydrogen atom or an optionally substituted $C_{1-10}$ alkyl or $C_{1-10}$ alkoxy group; and R³ and R⁴ independently represent a hydrogen atom or an optionally substituted $C_{1-10}$ alkyl or $C_{1-10}$ alkoxy group or R³ and R⁴ together represent an optionally substituted $C_{1-8}$ alkylene group; said process comprising the steps of reacting gaseous hydrogen chloride in the presence of a solvent with a compound of the formula

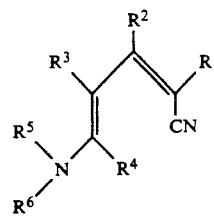
(II)

in which R, R², R³, and R⁴ are as defined above and R⁵ and R⁶ independently represent a hydrogen atom or an optionally substituted $C_{1-10}$ alkyl, $C_{2-10}$ alkenyl, $C_{2-10}$ alkynyl, $C_{3-10}$ cycloalkyl or aryl group or R⁵ and R⁶ together with the interjacent nitrogen atom represent an optionally substituted pyrrolidine ring, said optional substituents being selected from halogen atoms, nitro, cyano, hydroxyl, $C_{3-6}$ cycloalkyl, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, formyl, $C_{1-6}$ alkoxycarbonyl, carboxyl, $C_{1-6}$ alkanoyl, $C_{1-6}$ alkylthio, $C_{1-6}$ alkylsulphinyl, $C_{1-6}$ alkylsulphonyl, carbamoyl and $C_{1-6}$ alkylamino groups.

2. A process according to claim 1 wherein R represents the group —CONR¹R⁷ and R¹ and R⁷ independently represents a $C_{1-4}$ alkyl group.

3. A process according to claim 1 wherein R represents the group —SO₂R⁸ and R⁸ represents a $C_{1-4}$ alkyl group.

4. A process according to claim 1 wherein R² represents a hydrogen atom.

5. A process according to claim 1 wherein R³ represents a hydrogen atom.

6. A process according to claim 1 wherein R⁴ represents a hydrogen atom.

7. A process according to claim 1 wherein R⁵ and R⁶ independently represent a $C_{1-4}$ alkyl group.

8. A process according to claim 1 wherein the compound of formula II is generated in situ.

9. A process according to claim 1 wherein the reaction is carried out in the presence of an excess of hydrogen chloride.

* * * * *

UNITED STATES PATENT AND TRADEMARK OFFICE
CERTIFICATE OF CORRECTION

PATENT NO. : 5,206,372
DATED : April 27, 1993
INVENTOR(S) : Ludwig Schroder

It is certified that error appears in the above-indentified patent and that said Letters Patent is hereby corrected as shown below:

Column 5, line 29, after "hydrogen", insert --atom--;

Column 5, line 39, "$C_{14\ 10}$" should read --$C_{10-10}$--; and

Column 6, line 21-22, "alkyamino" should read --alkylamido--.

Signed and Sealed this

Fourth Day of January, 1994

Attest:

BRUCE LEHMAN

Attesting Officer

Commissioner of Patents and Trademarks